United States Patent
Smith

(10) Patent No.: US 10,169,851 B2
(45) Date of Patent: Jan. 1, 2019

(54) METHODS FOR COLOR ENHANCED DETECTION OF BONE DENSITY FROM CT IMAGES AND METHODS FOR OPPORTUNISTIC SCREENING USING SAME

(71) Applicant: COLOR ENHANCED DETECTION, LLC, Ridgeland, MS (US)

(72) Inventor: Andrew Dennis Smith, Ridgeland, MS (US)

(73) Assignee: COLOR ENHANCED DETECTION, LLC, Birmingham, AL (US)

( * ) Notice: Subject to any disclaimer, the term of this patent is extended or adjusted under 35 U.S.C. 154(b) by 0 days.

(21) Appl. No.: 15/863,514

(22) Filed: Jan. 5, 2018

(65) Prior Publication Data

US 2018/0322618 A1 Nov. 8, 2018

Related U.S. Application Data

(60) Provisional application No. 62/500,220, filed on May 2, 2017.

(51) Int. Cl.
*G06K 9/00* (2006.01)
*G06T 5/00* (2006.01)
(Continued)

(52) U.S. Cl.
CPC .............. *G06T 5/002* (2013.01); *A61B 6/032* (2013.01); *A61B 6/505* (2013.01); *A61B 6/5217* (2013.01);
(Continued)

(58) Field of Classification Search
None
See application file for complete search history.

(56) References Cited

U.S. PATENT DOCUMENTS 5,717,735 A * 2/1998 Ramsdell ............. A61B 6/0421
378/195
5,838,765 A * 11/1998 Gershman ............ A61B 6/0421
378/146

(Continued)

FOREIGN PATENT DOCUMENTS

WO 2014201052 A2 12/2014
WO WO 2014/201052 * 12/2014

*Primary Examiner* — Tahmina Ansari
(74) *Attorney, Agent, or Firm* — Workman Nydegger

(57) ABSTRACT

Embodiments describe an accurate and rapid method for assessing spinal bone density on chest or abdominal CT images using post-processed colored images. Post-processing of CT images for the purposes of displaying the spine is followed by color enhancement of routine unenhanced or contrast enhanced CT images to improve diagnostic accuracy, inter-observer agreement, reader confidence and/or time of interpretation as it relates to assessing bone density of the spine. CT images are post-processed (without changes to the standard-of-care CT imaging protocol and without additional cost or radiation for the patient) to straighten the spine for improved visualization of multiple segments. The color-enhanced images can be displayable simultaneously with the grayscale images. Methods and systems are provided for performing opportunistic bone density screening.

23 Claims, 6 Drawing Sheets
(3 of 6 Drawing Sheet(s) Filed in Color)

(51) Int. Cl.
*G06T 7/00* (2017.01)
*G06T 7/11* (2017.01)
*A61B 6/03* (2006.01)
*A61B 6/00* (2006.01)

(52) U.S. Cl.
CPC .......... *A61B 6/5258* (2013.01); *G06T 7/0012* (2013.01); *G06T 7/11* (2017.01); *G06T 2207/10081* (2013.01); *G06T 2207/30012* (2013.01)

(56) References Cited

U.S. PATENT DOCUMENTS

| | | |
|---|---|---|
| 9,747,700 B2 | 8/2017 | Smith |
| 2005/0094859 A1* | 5/2005 | Ruth .................... G06T 7/0012 382/132 |
| 2009/0016587 A1* | 1/2009 | Strobel ................ A61B 6/469 382/130 |
| 2009/0096807 A1* | 4/2009 | Silverstein ............ G06T 11/001 345/593 |
| 2013/0243298 A1* | 9/2013 | Bredno .................... G06T 5/50 382/131 |

* cited by examiner

METHODS FOR COLOR ENHANCED DETECTION OF BONE DENSITY FROM CT IMAGES AND METHODS FOR OPPORTUNISTIC SCREENING USING SAME

CROSS-REFERENCE TO RELATED APPLICATIONS

This application claims the benefit of U.S. Provisional Patent Application No. 62/500,220, filed May 2, 2017, the disclosure of which is incorporated herein by reference in its entirety.

BACKGROUND

Computed tomography (CT) imaging is a medical imaging procedure that utilizes X-rays and is used to generate diagnostic images of various body areas. Diagnostic CT images are obtained in the axial plane. Standard diagnostic images for clinical purposes are displayed in grayscale with various shades of black, gray and white. Grayscale CT images have been in use since commercialization of CT scanners in 1972. Pixel intensities are standardized and displayed according to the mean attenuation of the tissues in Hounsfield Units (HU). See Table 1. Each pixel represents a 3D volume of tissue known as a voxel. Radiodense contrast is frequently administered to patients via oral or intra-vascular routes to enhance detection of abnormalities.

Many, if not all, of diagnostic CT images are processed such that images can be displayed with slice thickness, field of view, smoothing kernel, windows, etc. so that imaging is optimized to the diagnostic clinical condition being evaluated. Windowing is a method for displaying a range of pixel intensities and is frequently used to look at a particular organ (e.g. brain vs. soft tissue vs. liver) or set of images for a specific imaging or clinical abnormality. Various forms of advanced processing and post-process of CT images are used to enhance diagnostic accuracy and decrease the complexity and time of interpretation of images by radiologists and other clinicians.

TABLE 1

Approximate Attenuation of Various Tissues and Substances in Hounsfield Units.

| Tissue/Substance | Attenuation (HU) |
| --- | --- |
| Air | −1000 to −950 |
| Fat | −190 to −30 |
| Fluid | −10 to 20 |
| White Matter | 25 to 35 |
| Acute Ischemic Brain Tissue | 20 to −35 |
| Gray Matter | 35 to −45 |
| Normal Artery | 45 to −55 |
| Hyperdense Artery | 55 to −100 |
| Acute Blood | 45 to 120 |
| Bone | 30 to 700 |
| Metal | >1000 |

Color is used to enhance image diagnosis in some CT image applications (e.g. volumetric and perfusion imaging) but is not used in routine CT imaging. With the advent of multi-detector CT and development of volume-rendered post-processed images, color was introduced to enhance display of the 3D volume-rendered CT images. Additional advances in CT imaging (e.g. CT angiography, CT perfusion, hybrid imaging (PET CT and SPECT CT), and dual energy CT) have increased the usage of colors in post-processed CT imaging studies. The purpose of the color displays in most CT image applications is to either enhance viewing of 3D structures, to summarize large volumes of data in a series of images (e.g. CT perfusion imaging), or to overlay two different types of imaging for hybrid display (e.g. PET CT imaging).

Osteoporosis is a common, silent disease that is frequently underdiagnosed and undertreated until a fracture occurs. Osteoporosis contributes to 1.5 million annual fractures in the U.S., and its incidence and prevalence is growing. Approximately 1 in 2 postmenopausal women and 1 in 5 older men are at risk for an osteoporosis-related fracture, and approximately 10 million Americans have osteoporosis. There are significant healthcare and economic costs and a surprisingly high morbidity and mortality associated with osteoporotic fractures.

Screening is essential for the prevention of osteoporotic fractures but is currently underutilized, with more than half of osteoporotic fractures occurring in patients that were never screened. The most common method used to screen for osteoporosis is dual energy x-ray absorptiometry (DXA). DXA is a safe, reliable, noninvasive, relatively inexpensive x-ray method for measuring bone density of the lumbar spine or hips. The DXA device is small but often not available at most point-of-care facilities.

Opportunistic screening for abnormal bone density (osteoporosis and low bone density) using routine abdominal computed tomography (CT) images obtained for other purposes offers a potential solution to improve screening efforts. In 2014, there were approximately 81 million CT scans performed in the U.S. The majority (>60M) of these CT scans include images of the spine and contain useful information about bone density. Opportunistic screening using routine abdominal CT scans obtained for other clinical indications offers numerous advantages, as it requires no additional cost, patient time, scanner equipment, or radiation exposure. There are several potential methods for assessing spinal bone density on routine abdominal CT images for the purposes of opportunistic screening. An ideal opportunistic screening method for detecting abnormal bone density on routine abdominal CT images would be accurate, rapid, and have high inter-observer agreement.

Quantitative Computed Tomography (QCT) is a specialized procedure whereby spinal bone density is measured in reference to a phantom containing different concentrations of bone-simulating material. QCT provides an accurate measure of spinal bone density, with avoidance of osteophytes and other confounders, and has high inter-observer agreement. However, measurement of spinal bone density requires advanced post-processing software, and the processing of data is labor intensive and time consuming. By comparison, visual assessment of routine abdominal CT images to subjectively screen for abnormal bone density of the spine offers a potentially rapid method but is associated with poor accuracy and poor inter-observer agreement.

A recently proposed opportunistic screening method that utilizes routine abdominal CT images includes measurement of trabecular bone attenuation at L1 on a single sagittal reconstruction image. While this approach has been validated using DXA as a reference standard, this method has not been validated with QCT as a reference standard. Furthermore, a single attenuation measurement at L1 on reconstructed images with 3 mm section thickness may not accurately represent the true bone density at L1 or at other spinal levels due to the relative heterogeneity of bone density in the spine. Despite the fact that this method is relatively accurate and rapid, it is rarely used in clinical practice for the following reasons: it requires the user to remember to make the measurement when the purpose of the abdominal CT was for something different than bone density screening, it requires a number of mouse clicks and scrolling to prepare the image for measurement, and it requires additional time for interpretation of the quantitative information.

Because current methods for opportunistic bone density screening utilizing routine abdominal CT images have a number of pitfalls, there is a need for an accurate, rapid, and reproducible technique to screen for abnormal bone density on routine abdominal CT images that include the spine.

BRIEF SUMMARY

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature (s) mentioned; likewise, those features can be applied to other embodiments of the presently-disclosed subject matter, whether listed in this summary or not. To avoid excessive repetition, this summary does not list or suggest all possible combinations of features.

One objective of this disclosure is to describe an accurate and rapid method for detecting abnormal spinal bone density on abdominal CT images using post-processed colored images. In some embodiments, post-processing of CT images for the purposes of segmentation and standardization followed by color enhancement of routine unenhanced or contrast enhanced CT images can potentially improve diagnostic accuracy, inter-observer agreement, reader confidence and/or time of interpretation. CT images can be post-processed (without changes to the standard-of-care CT imaging protocol and without additional cost or radiation for the patient) for segmentation, standardization, and color-enhancement techniques. The color-enhanced images can be displayed simultaneously with the grayscale images for a side-by-side comparison. The use of color-enhanced CT images to improve perception or diagnostic accuracy can be referred to as Color Enhanced Detection (CED).

The present disclosure provides, in certain embodiments, a method of opportunistic bone density screening. In some embodiments, the method comprises the steps of: (i) receiving, in an image processor, digital computed tomography (CT) image data obtained by a digital image capture device, wherein the digital image data comprises at least one medical image; (ii) processing the digital image data with the image processor to obtain a straightened thick slab sagittal image of the midline spine; (iii) providing a color palette, wherein a plurality of colors are each related to a specific range of attenuation values (i.e., pixel intensities); wherein each range of attenuation values therein corresponds to different bone density conditions; and (iv) mapping the selected color palette to straightened thick slab sagittal image of the spine in order to screen for abnormal bone density conditions.

In some embodiments, the spine is segmented from the input image data set, and the color palette is mapped to the segmented image of the spine. Thereby only the spine is colored on the final image. In other embodiments, only the trabecular bone of the vertebral bodies is segmented, and the color palette is mapped to the segmented image of the trabecular bone of the vertebral bodies. In other embodiments, the cortical bone and trabecular bone of the spine are separately segmented and separately colored.

In some embodiments, a plurality of colored images of the spine are generated. The plurality of images may all have the same color palette applied, or they may have different color palettes applied to identify different bone density conditions.

In some embodiments, the spinal images are colored to enhance detection of pathologic findings such as metastases or other bone lesions. The colors may be used to differentiate benign bone findings from potentially malignant or pathologic bone findings.

In some embodiments, the digital image data is processed with the image processor (which can be a hardware or software image processor or a combination thereof), and such processing may comprise applying at least one of a noise reduction filter or smoothing algorithm. The smoothing algorithm is designed to provide a more homogenous image and better represent the average bone density (or average bone attenuation) of the individual vertebral bodies. The smoothing algorithm may comprise a Gaussian smoothing algorithm in certain embodiments, but other smoothing algorithms can be used. In some embodiments, the color spectrum can be saved in a bank and/or a data storage area (e.g., in volatile or nonvolatile storage, which can be stored locally or distributed).

In some embodiments, abnormal bone density is defined as greater than about 30 Hounsfield Units (HU) and less than about 145 HU, and normal bone density is defined as greater than or equal to about 145 HU and less than about 700 HU. In other embodiments, abnormal bone density is defined as greater than about 30 HU and less than about 95 HU, and normal bone density is defined as greater than or equal to about 95 HU and less than about 700 HU. In other embodiments, osteoporosis is defined as greater than about 30 HU and less than about 95 HU, low bone density is defined as greater than or equal to 95 HU and less than about 145 HU, and normal bone density is defined as greater than or equal to about 145 HU and less than about 700 HU.

It should be appreciated that the image processor can identify the pixel intensity of each or at least of a plurality of pixels and associate a pixel intensity value (e.g., in HU) with each identified pixel intensity. The identified pixel intensities can, in some embodiments, be ordered, flagged, or otherwise notated (e.g., within metadata associated with the image file) for association with one or more colors selected from a color palette.

In some embodiments, the color palette comprises at least two colors. In some embodiments, abnormal bone density is colored red and normal bone density is colored green (e.g., pixels having an intensity greater than about 30 HU and less than about 144 HU are colored red and pixels having an intensity greater than or equal to about 145 and less than about 700 HU are colored green; pixels having an intensity falling outside of the range of 30-700 HU can be illustrated in grayscale, omitted from the image, or provided a different color). In other embodiments, osteoporosis is colored red, low bone density is colored blue, and normal bone density is colored green. It is understood that a variety of color choices or grayscale intensities can be used to identify various bone density conditions, and the choice of colors or grayscale intensities can be chosen by the end user, with a variety of suggestions made available but also allowing for full customization by the end user.

In some embodiments, the image processor can straighten the spine (e.g., align the vertebrae in a co-localized plane) to obtain a thick slab sagittal image of the midline spine. Some patients have straight spines but may be misaligned relative to the scanner table or true sagittal image axis, whereby a true sagittal image would not show the entire extent of the spine. The image processor may be used to align the spine such that a single thick slab sagittal image of the midline spine is generated. In patients who have scoliosis or curvatures of the spine, the image processor can straighten the spine and remove the curvature to obtain a thick slab sagittal image of the midline spine.

In some embodiments, the thick slab sagittal image of the spine can be a reconstruction of the average pixel intensities in a 20 mm section representing the midline of the vertebral body. In other embodiments, the section thickness can vary between 0.6 mm and the full thickness of the vertebral body. In still other embodiments, multiple images of the spine can be created, each with a different section thickness. In still other embodiments, additional reconstructions of the spine can be generated and colored including minimum and maximum intensity projections, 3D and volumetric reconstructions, and/or a variety of other reconstructions. It is understood that the color techniques can be applied to a variety or reconstructions of the spine and can be applied to other views (e.g. coronal, axial, or oblique views).

In some embodiments, the source data (digital medical images) can include imaging data of the neck, chest, abdomen, pelvis, or any other CT image including the spine or a portion thereof. It is understood that the image processor can function with complete or partial images of the spine (e.g. full body CT vs. limited imaging of a portion of the body).

Additionally, the methods of the present disclosure may comprise a step of analyzing the digital image data, including determining at least one statistical measure of the digital image data (e.g., by a processor). The statistical measure may be, for example, an arithmetic mean of the at least one pixel intensity value of at least one pixel in the region of interest. Also, in some embodiments, the statistical measurement can be restricted to a range of pixel intensities, not including all possible pixel intensities (e.g., the gated pixel intensities described above).

It should be appreciated that the present disclosure provides numerous benefits over that which is known and practiced in the art. For example, applications of the present disclosure can reduce the time to identify an abnormality, can increase the accuracy of positively identifying an abnormality, and/or more acutely specify the abnormality with respect to location and/or severity. The present disclosure can allow for a rapid and accurate assessment of bone density in multiple vertebral bodies, which can then potentially be used to guide therapy (e.g. noninvasive medical vs. vertebroplasty or kyphoplasty).

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be apparent to one of ordinary skill in the art from the description, or may be learned by the practice of the teachings herein. Features and advantages of embodiments described herein may be realized and obtained by means of the instruments and combinations particularly pointed out in the appended claims. Features of the embodiments described herein will become more fully apparent from the following description and appended claims.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

To further clarify the above and other features of the embodiments described herein, a more particular description will be rendered by reference to the appended drawings. It is appreciated that these drawings depict only examples of the embodiments described herein and are therefore not to be considered limiting of its scope. The embodiments will be described and explained with additional specificity and detail through the use of the accompanying drawings in which.

DETAILED DESCRIPTION

Figure 1:
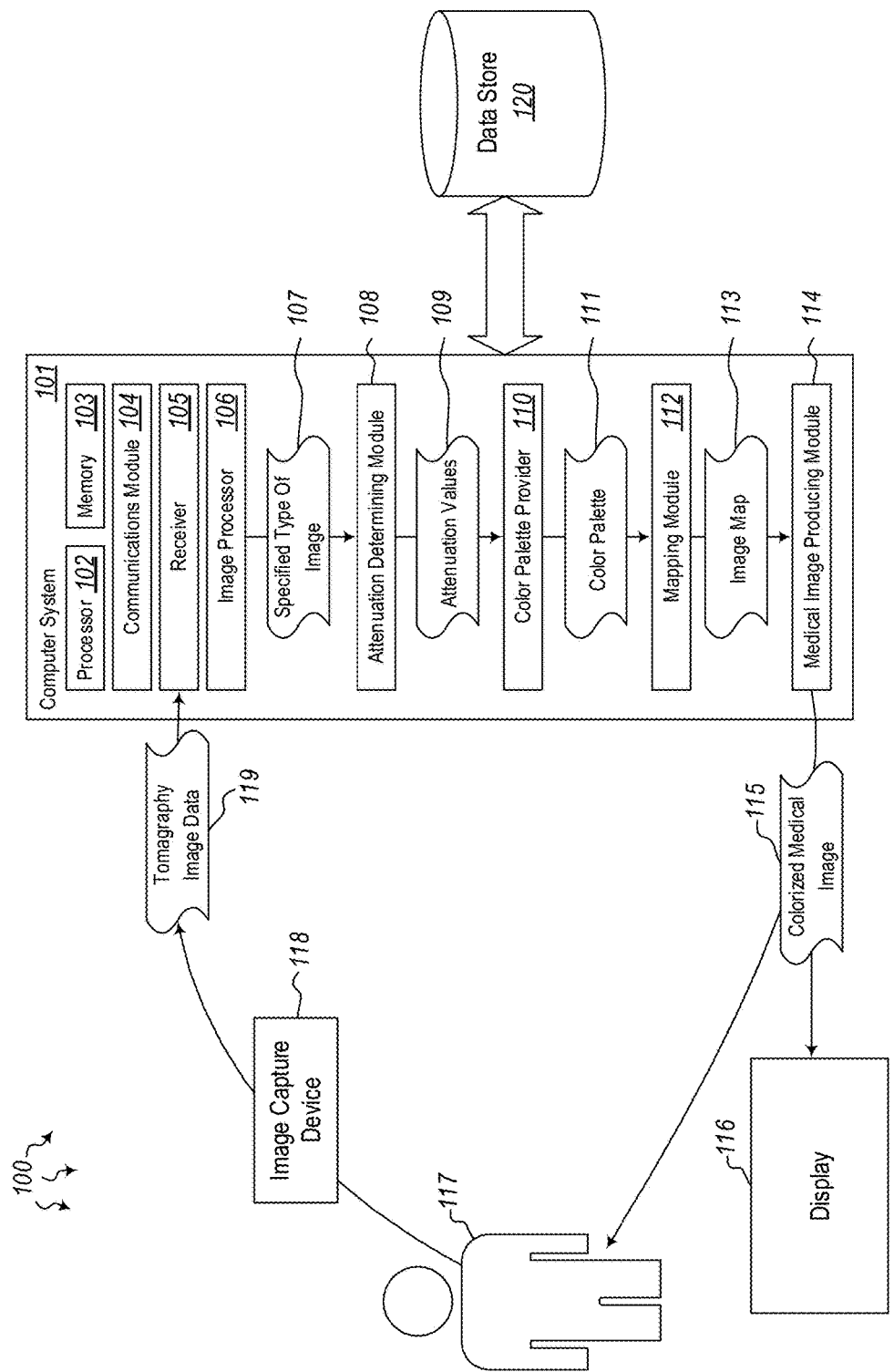
FIG. 1 schematically illustrates a computer architecture in which embodiments described herein may operate, including performing opportunistic bone density screening.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Each example is provided by way of explanation of the present disclosure and is not a limitation thereon. In fact, it will be apparent to those skilled in the art that various modifications and variations can be made to the teachings of the present disclosure without departing from the scope of the disclosure. For instance, features illustrated or described as part of one embodiment can be used with another embodiment to yield a still further embodiment.

All references to singular characteristics or limitations of the present disclosure shall include the corresponding plural characteristic(s) or limitation(s) and vice versa, unless otherwise specified or clearly implied to the contrary by the context in which the reference is made. All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional components or limitations described herein or otherwise useful. While the terms used herein are believed to be well understood by one of ordinary skill in the art, some definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "an imaging study" includes a plurality of such images, and so forth. Unless otherwise indicated, all numbers expressing quantities, properties, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The terms "subject," "individual" and "patient" are used interchangeably throughout the present disclosure. In some embodiments, each of these terms refers to a vertebrate, preferably a mammal, more preferably a human. The phrases "pixel intensity", "pixel intensity value", and "pixel value" are used interchangeably throughout the present disclosure, wherein a pixel value is a measure of the signal intensity of a voxel in an image. The phrase "corresponds to" or "corresponding to" may be used, variously, to imply equivalence, equality, and/or values approximate to equivalence and/or equality. In some embodiments, "corresponds to" or "corresponding to" is used interchangeably with "about" and/or "that is about."

FIG. 1 illustrates a computer architecture 100 in which at least one embodiment described herein may be employed. The computer architecture 100 includes a computer system 101. The computer system 101 includes at least one processor 102 and at least some system memory 103. The computer system 101 may be any type of local or distributed computer system, including a cloud computer system. The computer system 101 includes modules for performing a variety of different functions. For instance, communications module 104 may be configured to communicate with other computer systems. The communications module 104 may include any wired or wireless communication means (e.g. hardware radios such as WiFi, Bluetooth, cellular, or GPS radios) that can receive and/or transmit data to or from other computer systems or transceivers. The communications module 104 may be configured to interact with databases, mobile computing devices (such as mobile phones or tablets), embedded computer systems or other types of computer systems.

The receiver 105 may be a separate module within computer system 101, or may be part of communications module 104. The receiver is configured to receive or otherwise access tomography image data 119. This tomography image data may be digital image data received from image capture device 118 (e.g. a CT scanner). Optionally, this tomography image data 119 may be stored in data store 120, and accessed at a later time if needed. The tomography image data 119 may include data for a single patient or for multiple patients. The receiver 105 passes the tomography image data 119 to an image processor 106 that is configured to process the image data. The image processor 106 may be the same as or different than the processor 102 of computer system 101. The image processor includes hardware, firmware and/or software that process the image 119 to form a specified type of image. In some embodiments herein, the specified type of image may be a medical image. More specifically, it may be a medical image of a specific part of a patient's body. For example, in one specific case, the medical image may be a straightened sagittal image of the patient's midline spine. This processed image 107 may then be sent to the attenuation determining module 108. The attenuation determining module may be configured to analyze the image 107 to determine where attenuation of the X-rays (or other imaging rays) has occurred. All or part of the image is analyzed to identify attenuation values 109 where attenuation has occurred.

Figure 2:
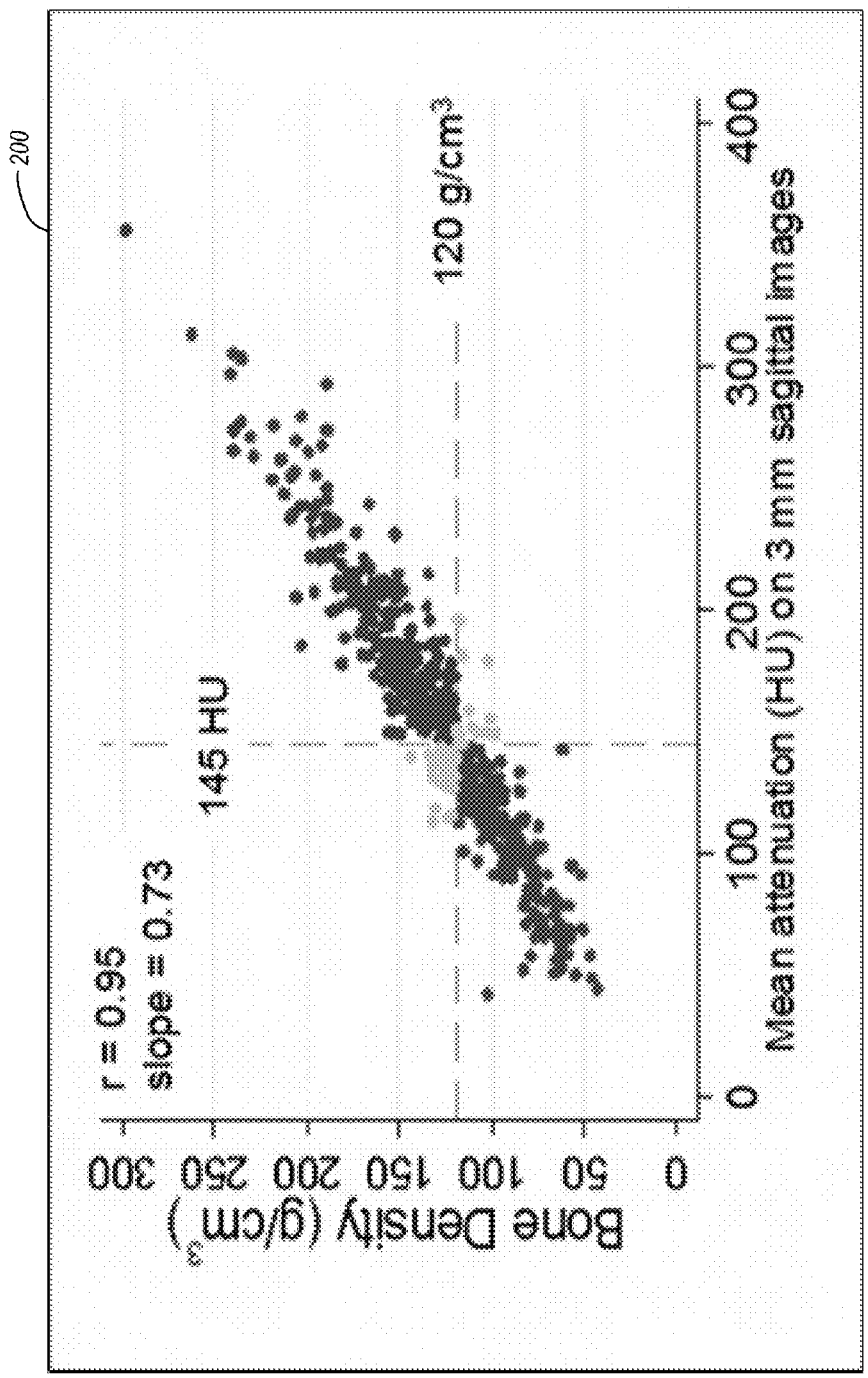
FIG. 2 is a scatter chart showing a high correlation between vertebral body mean attenuation and bone density as measured by quantitative computed tomography.

FIG. 2 shows a graph 200 illustrating example attenuation data for sagittal images. The x-axis of graph 200 shows mean attenuation in sagittal images, and the y-axis shows bone density. As can be seen in graph 200, attenuation begins to occur at roughly 48 $g/cm^3$ and persists along a nearly linear slope up to 300 $g/cm^3$. Lower values (indicating abnormal bone density levels) are shown in red, midrange values are shown in yellow, and higher values (indicated normal bone density levels) are shown in green. FIG. 2 thus shows a high correlation between vertebral body mean attenuation and bone density as measured by quantitative computed tomography. In at least some embodiments, the cut point of 145 HU can be used to differentiate normal bone density from abnormal bone density. Once the attenuation values have been identified, a color palette provider 111 provides a color palette 111 to a mapping module 112 that maps one or more colors of the palette to an image map 113. The image map 113 may include an indication of which pixels or voxels are to be colored, and which colors are to be represented.

Figure 3:
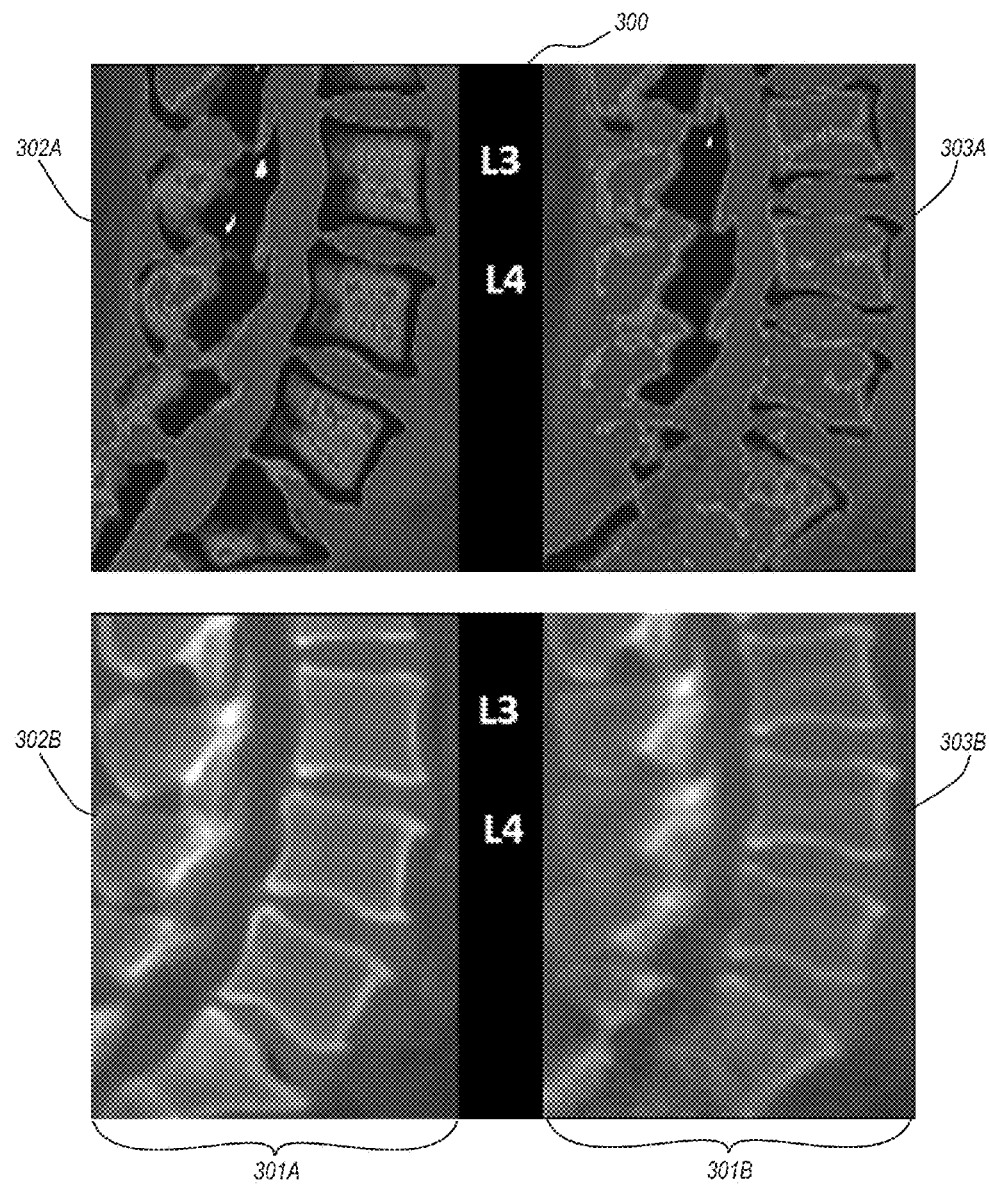
FIG. 3 illustrates colored and grayscale straightened thick slab sagittal images of the midline spine from patients with normal bone density (green) on the left and abnormal bone density (red) on the right.

FIG. 3 illustrates a collection of example images 300. The collection represents two different patients: the left side represents one patient (301A) having a colored image 302A and a grayscale image 302B. The right side represents another patient (301B) having a colored image 303A and a grayscale image 303B. Patient 301A's colored and grayscale images are straightened thick slab sagittal images of the midline spine from a patient with normal bone density. In FIG. 3, this is shown in green, although another color may be used. Patient 301B's colored and grayscale images are also straightened thick slab sagittal images of the midline spine, but from a patient with abnormal bone density. This is shown in red in FIG. 3. With the image map 113 created, the medical image producing module 114 may generate a colorized medical image 115. This colorized medical image 115 may be sent to a user (e.g. 117), to a display (e.g. 116), to a data store 120, or to some other location. The colorized medical image 115 represents an image of a particular region of a patient's body. In one embodiment, the colorized medical image 115 is an image of a patient's spine.

Figure 4:
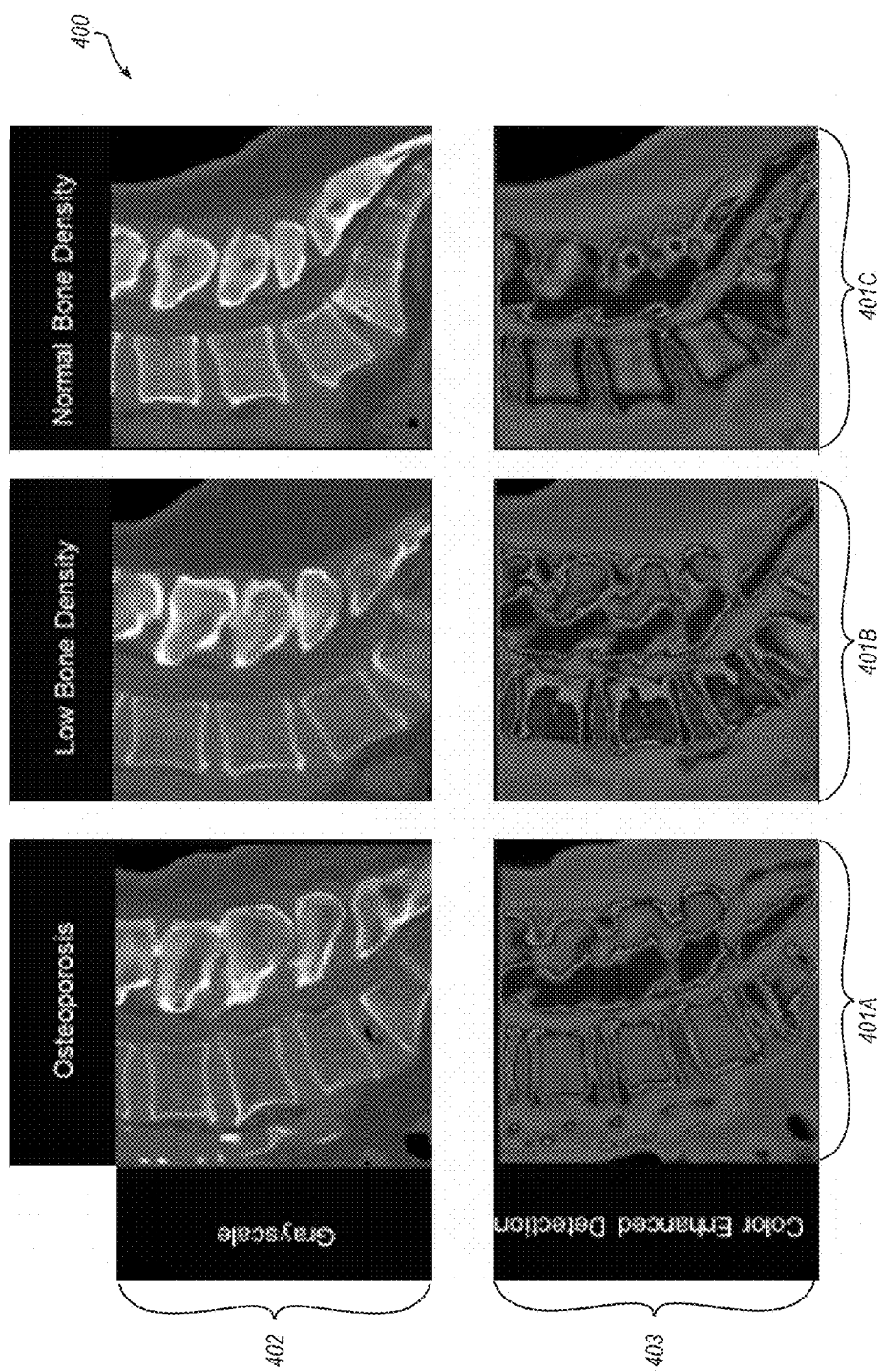
FIG. 4 illustrates colored and grayscale straightened thick slab sagittal images of the midline spine from patients with osteoporosis (red) on the left, low bone density (blue) in the middle, and normal bone density (green) on the right.

FIG. 4 illustrates an example collection of images 400. Grayscale images 402 are shown for three different patients (401A-401C) in the upper portion of the collection, while color-enhanced detection images 403 are shown in the bottom portion. As can be seen from the images for each patient, patient 401A has a relatively high amount of red coloring in the trabecular bone, indicating signs of osteoporosis. Patient 401B's color-enhanced image shows a relatively high amount of blue coloring in the trabecular bone, indicating signs of low bone density. Patient 401C's color-enhanced image shows a higher amount of green color in the trabecular bone, indicating a healthy patient with normal bone density. These colorized images may be generated from CT scan data or from other data sources. This will be explained further below.

Figure 5:
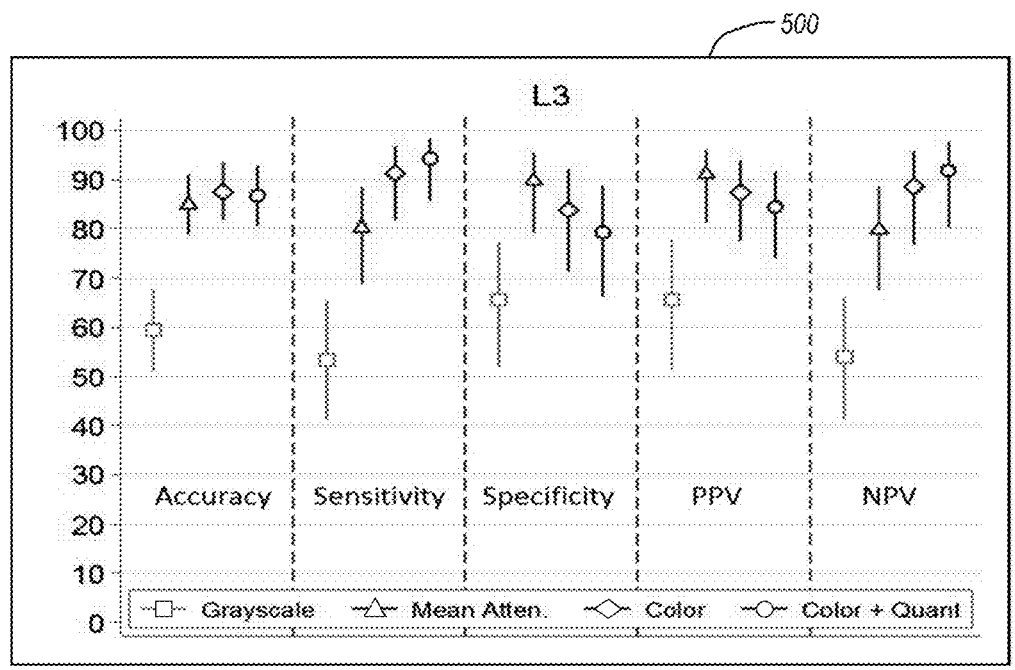
FIG. 5 is a graph that shows the average accuracy, sensitivity, specificity, and positive and negative predictive values of grayscale, mean attenuation, colored images, and color+quantitative measures for five readers assessing bone density on CT images from 120 different patients.

FIG. 5 shows a chart 500 that illustrates actual data from 120 different patients. Specifically, chart 500 shows the average accuracy, sensitivity, specificity, and positive and negative predictive values of grayscale, mean attenuation, colored images, and color+quantitative measures for five readers assessing bone density on CT images from 120 different patients. As can be seen from the chart 500, the accuracy was highest using the color enhanced detection method.

Figure 6:
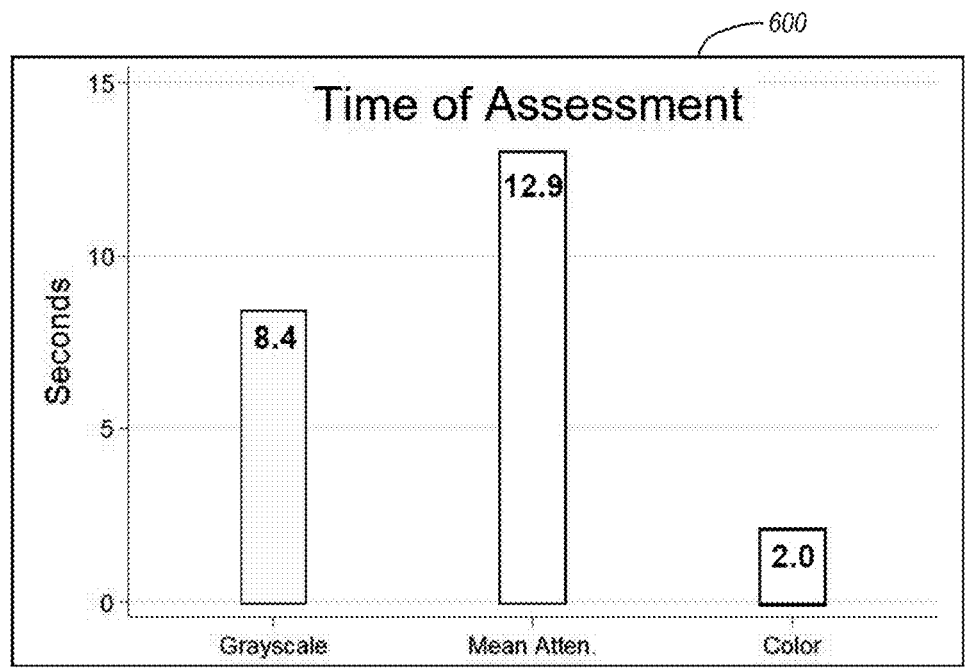
FIG. 6 is a bar chart that shows the average time of interpretation of grayscale, mean attenuation, and colored images for five readers assessing bone density on CT images from 120 different patients.

FIG. 6 shows a chart 600 that illustrates the average time of interpretation of grayscale, mean attenuation, and colored images for five readers assessing bone density on CT images from 120 different patients. The average time of two seconds was fastest using the color enhanced detection method. Such data may be obtained using one or more of the methods, systems and computer program products described herein.

Figure 7:
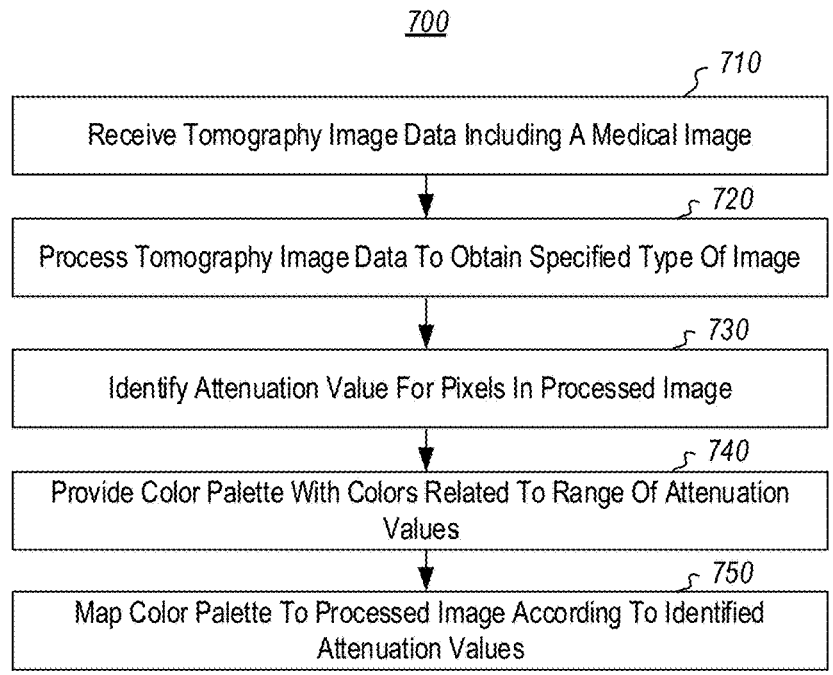
FIG. 7 is a flowchart that illustrates an example method for performing opportunistic bone density screening.

In view of the systems and architectures described above, methodologies that may be implemented in accordance with the disclosed subject matter will be better appreciated with reference to the flow chart of FIG. 7. For purposes of simplicity of explanation, the methodologies are shown and described as a series of blocks. However, it should be understood and appreciated that the claimed subject matter is not limited by the order of the blocks, as some blocks may occur in different orders and/or concurrently with other blocks from what is depicted and described herein. Moreover, not all illustrated blocks may be required to implement the methodologies described hereinafter.

FIG. 7 more particularly shows a flowchart that illustrates a method 700 for performing opportunistic bone density screening. The method 700 will be described with frequent reference to the components and data of environment 100 of FIG. 1. Method 700 includes the step 710 of receiving, at an image processor, one or more portions of tomography image data obtained using an image capture device, the tomography image data including an image of at least a portion of a patient's body. For example, receiver 105 or image processor 106 may receive or otherwise access tomography image data 119. This tomography image data 119 is then processed in step 720 by the image processor 106 to obtain a specified type of image relevant for that portion of the patient's body. In one example, the tomography image data 119 is digital data from a digital image capture device. This digital tomography image data may include one or more medical image used for the purposes of diagnosing an illness or disease.

As shown in FIGS. 2-4, the specified type of image is a medical image that represents a straightened sagittal image of the patient's midline spine. Although a patient's spine is used as an example herein, it will be recognized that substantially any part or portion of the patient's body may be represented by the tomography image data 119.

Returning to FIG. 7, method 700 next includes a step 730 of identifying an attenuation value for one or more pixels in the processed image. The attenuation determining module 108 is configured to identify attenuation values of pixels or voxels associated with the medical (or other type of) image 107. The attenuation determining module 108 may use various algorithms or formulas to determine where the electromagnetic rays used to generate the tomography image data 119 were attenuated when passing through the patient's body. Different levels of attenuation may mean different things to doctors. In some cases, as noted above, attenuation can indicate different levels of bone density. These different levels of bone density can, in turn, indicate osteoporosis or other bone diseases in the patient. The various levels of bone density are assigned a specific color for presentation to doctors or other caregivers, as outlined in method steps 740 and 750.

Indeed, step 740 of method 700 includes providing a color palette comprising one or more colors, where the one or more colors are each related to a specific range of attenuation values, and where each specific range of attenuation values corresponds to one or more different bone density conditions. The color palette provider 110 may provide color palette 111 with one or more colors to the mapping module 112. The color palette provider 110 may be its own hardware, software, or firmware module (or some combination thereof), and may provide different color palettes in different situations. For instance, some doctors or caregivers may have their own preferred color palettes. In such cases, the mapping module will use those color palettes. Some organizations (e.g. hospitals or doctor groups) may use their own specific color palette, or palettes may be standardized for certain types of medicine. For instance, it may become standard to color abnormal bone density in red, and normal bone density in green.

Once the appropriate color palette 111 has been selected and provided to the mapping module 112, the mapping module maps the provided color palette to the processed image 107 according to the identified attenuation values 109 to screen for abnormal bone density conditions (750). The medical image producing module 114 may generate a representation that includes the colorized medical image 115. This colorized image is colorized based on the attenuation values 198 and the image map 113 generated using the color palette 111. The colorized image 115 may be shown on a local display 116, or may be sent to a mobile device (e.g. a mobile phone, tablet or wearable device) or to data store 120. Using the colorized medical image, doctors or other caregivers can diagnose conditions related to patient's body parts, and provide a better informed opinion on the patient's current state of health.

Another embodiment described herein provides a more specific method of opportunistic bone density screening. The method may comprise the steps of: (i) receiving, in an image processor, digital computed tomography image data obtained by a digital image capture device, wherein the digital image data comprises at least one medical image; (ii) processing the digital image data with the image processor to obtain a straightened thick slab sagittal image of the midline spine; (iii) providing a color palette, wherein a plurality of colors are each related to a specific range of attenuation values (pixel intensities); wherein each range of attenuation values therein corresponds to different bone density conditions; (iv) mapping the selected color palette straightened thick slab sagittal image of the spine in order to screen for abnormal bone density conditions.

The digital image data comprises at least one image. In certain embodiments, the at least one image is a two-dimensional image. In certain embodiments, the digital image is a three-dimensional image. In some embodiments, the digital image data comprises at least one medical image, such as a cross sectional digital medical image. Accordingly, in certain embodiments, the digital image data comprises a plurality of digital medical images, such as cross sectional digital medical images of at least one portion of the body of a subject. The digital image data and/or a medical image of the present disclosure may comprise, in some embodiments, at least one of a computed tomography image. And in some embodiments, the digital image comprises a medical image obtained with the use of one or more contrast agents and/or radionuclides. The most common format for cross sectional digital medical images is the Digital Imaging and Communications in Medicine (DICOM) format. In another embodiment, other image formats, including, for example, JPEG, PNG, TIFF, and the like, could be processed via the methods of the present disclosure.

In some embodiments, the spine is segmented from the input image data set, and the color palette is mapped to the segmented image of the spine. Thereby only the spine is colored on the final image. In other embodiments, only the trabecular bone of the vertebral bodies is segmented, and the color palette is mapped to the segmented image of the trabecular bone of the vertebral bodies. In other embodiments, the cortical bone and trabecular bone of the spine are separately segmented and separately colored.

In some embodiments, multiple colored images of the spine are generated. The plurality of images may all have the same color palette applied (e.g. palette 111) or may have different color palettes applied to identify different bone density conditions. In some embodiments, the spinal are colored to enhance detection of pathologic findings such as metastases or other bone lesions. The colors may be used to differentiate benign bone findings from potentially malignant or pathologic bone findings.

In some embodiments, the digital image data is processed with the image processor 106, and the processing step may comprise applying at least one of a noise reduction filter and a smoothing algorithm. The smoothing algorithm is designed to provide a more homogenous image and better represent the average bone density (or average bone attenuation) of the individual vertebral bodies. The smoothing algorithm may comprise a Gaussian smoothing algorithm in certain embodiments, but may other smoothing algorithms could be used. And in some embodiments, the color spectrum is saved in a bank and/or a data storage area.

In some embodiments, abnormal bone density can be defined as greater than about 30 Hounsfield Units (HU) and less than about 145 HU, and normal bone density can be defined as greater than or equal to about 145 HU and less than about 700 HU. In other embodiments, abnormal bone density can be defined as greater than about 30 HU and less than about 95 HU, and normal bone density can be defined as greater than or equal to about 95 HU and less than about 700 HU. In other embodiments, osteoporosis can be defined as greater than about 30 HU and less than about 95 HU, low bone density can be defined as greater than or equal to 95 HU and less than about 145 HU, and normal bone density can be defined as greater than or equal to about 145 HU and less than about 700 HU.

In some embodiments, the color palette 111 comprises at least two colors. In some embodiments, abnormal bone density can be colored red and normal bone density colored green. In other embodiments, osteoporosis can be colored red, low bone density colored blue, and normal bone density colored green. It is understood that a variety of color choices could be used to identify various bone density conditions, and the choice of colors could be chosen by the end user, with a variety of suggestions made available but also allowing for full customization by the end user.

In some embodiments, the image processor 106 can straighten the spine to obtain a thick slab sagittal image of the midline spine. Some patients have straight spines but may be misaligned relative to the scanner table or true sagittal image axis, whereby a true sagittal image would not show the entire extent of the spine. The image processor 106 may be used to align the spine such that a single thick slab sagittal image of the midline spine is generated. Other patients have scoliosis or curvatures of the spine. The image processor 106 can straighten the spine and remove the curvatures to obtain a thick slab sagittal image of the midline spine.

Figure 8:
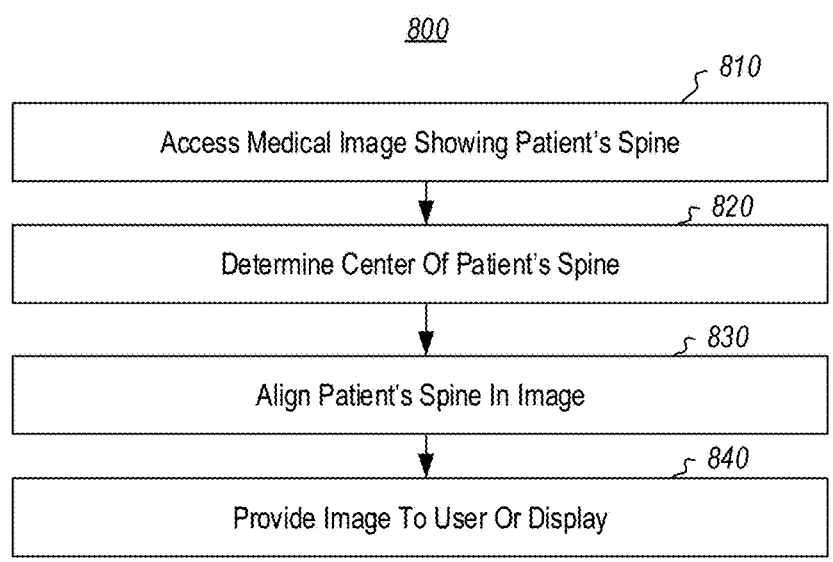
FIG. 8 is a flowchart that illustrates an example method for producing a straightened sagittal image of a patient's midline spine.

An example process of straightening the spine is described with reference to method 800 of FIG. 8. In method 800, an image processor (e.g. image processor 106 of FIG. 1) may, in step 810, access a medical image (e.g. a CT image) showing all or a portion of a patient's spine. Upon accessing the medical image, the image processor 106 may perform one or more calculations in step 820 to determine the center of the patient's spine. The term "center" here may refer to a longitudinal center relative to a longitudinal axis, or to a radial center relative to the radial center of each vertebra, or to both the longitudinal and radial centers. Using the calculated center of the patient's spine, the image processor 106 may in step 830 align the pixels or voxels representing the patient's spine to a center line. This aligned image is then provided in step 840 to a user directly or displayed on a display (e.g. display 116).

In some embodiments, after the patient's spine has been digitally straightened in the medical image, the mapping module 112 of FIG. 1 may map a specified color palette 111 to the image according to an image map 113. Thus, a straightened (colorized) sagittal image of the patient's midline spine may be generated and displayed for view by a medical professional. By providing an image with a straightened spine (as opposed to a curved spine), medical professional may have a better view of potential problems or abnormalities that may exist in the patient's spine. This leads to a better diagnosis and better patient care.

In some embodiments, the thick slab sagittal image of the spine can be a reconstruction of the average pixel intensities in a 20 mm section representing the midline of the vertebral body. In other embodiments, the section thickness can vary between 0.6 mm and the full thickness of the vertebral body. In still other embodiments, multiple images of the spine can be created, each with a different section thickness. In still other embodiments, additional reconstructions of the spine can be generated and colored including minimum and maximum intensity projections, 3D and volumetric reconstructions, and a variety of other reconstructions. It is understood that the color techniques can be applied to a variety or reconstructions of the spine and can be applied to other views (e.g. coronal, axial, and oblique views).

In some embodiments, the source data 119 (e.g. tomography medical images) can include the neck, chest, abdomen, pelvis or any CT image including the spine. It is understood that the image processor 106 can function with complete or partial images of the spine (e.g. full body CT vs. limited imaging of a portion of the body). Additionally, the methods of the present disclosure may comprise a step of analyzing the digital image data, including determining at least one statistical measure of the digital image data. The statistical measure may be, for example, an arithmetic mean of the at least one pixel intensity value of at least one pixel in the region of interest. Also, in some embodiments, the statistical measurement may be restricted to a range of pixel intensities, not including all possible pixel intensities.

Embodiments of the present invention may comprise or utilize a special-purpose or general-purpose computer system that includes computer hardware, such as, for example, one or more processors and system memory, as discussed in greater detail below. Embodiments within the scope of the present invention also include physical and other computer-readable media for carrying or storing computer-executable instructions and/or data structures. Such computer-readable media can be any available media that can be accessed by a general-purpose or special-purpose computer system. Computer-readable media that store computer-executable instructions and/or data structures are computer readable hardware storage devices. Computer-readable media that carry computer-executable instructions and/or data structures are transmission media. Thus, by way of example, and not limitation, embodiments of the invention can comprise at least two distinctly different kinds of computer-readable media: computer readable hardware storage devices and transmission media.

Computer readable hardware storage devices are physical storage media that store computer-executable instructions and/or data structures. Physical storage media include computer hardware, such as RAM, ROM, EEPROM, solid state drives ("SSDs"), flash memory, phase-change memory ("PCM"), optical disk storage, magnetic disk storage or other magnetic storage devices, or any other hardware storage device(s) which can be used to store program code in the form of computer-executable instructions or data structures, which can be accessed and executed by a general-purpose or special-purpose computer system to implement the disclosed functionality of the invention.

Transmission media can include a network and/or data links which can be used to carry program code in the form of computer-executable instructions or data structures, and which can be accessed by a general-purpose or special-purpose computer system. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer system, the computer system may view the connection as transmission media. Combinations of the above should also be included within the scope of computer-readable media.

Further, upon reaching various computer system components, program code in the form of computer-executable instructions or data structures can be transferred automatically from transmission media to computer readable hardware storage devices (or vice versa). For example, computer-executable instructions or data structures received over a network or data link can be buffered in RAM within a network interface module (e.g., a "NIC"), and then eventually transferred to computer system RAM and/or to less volatile computer readable hardware storage devices at a computer system. Thus, it should be understood that computer readable hardware storage devices can be included in computer system components that also (or even primarily) utilize transmission media.

Computer-executable instructions comprise, for example, instructions and data which, when executed at one or more processors, cause a general-purpose computer system, special-purpose computer system, or special-purpose processing device to perform a certain function or group of functions. Computer-executable instructions may be, for example, binaries, intermediate format instructions such as assembly language, or even source code.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The invention may also be practiced in distributed system environments where local and remote computer systems, which are linked (either by hardwired data links, wireless data links, or by a combination of hardwired and wireless data links) through a network, both perform tasks. As such, in a distributed system environment, a computer system may include a plurality of constituent computer systems. In a distributed system environment, program modules may be located in both local and remote memory storage devices.

Those skilled in the art will also appreciate that the invention may be practiced in a cloud-computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

A cloud-computing model can be composed of various characteristics, such as on-demand self-service, broad network access, resource pooling, rapid elasticity, measured service, and so forth. A cloud-computing model may also come in the form of various service models such as, for example, Software as a Service ("SaaS"), Platform as a Service ("PaaS"), and Infrastructure as a Service ("IaaS"). The cloud-computing model may also be deployed using different deployment models such as private cloud, community cloud, public cloud, hybrid cloud, and so forth.

Some embodiments, such as a cloud-computing environment, may comprise a system that includes one or more hosts that are each capable of running one or more virtual machines. During operation, virtual machines emulate an operational computing system, supporting an operating system and perhaps one or more other applications as well. In some embodiments, each host includes a hypervisor that emulates virtual resources for the virtual machines using physical resources that are abstracted from view of the virtual machines. The hypervisor also provides proper isolation between the virtual machines. Thus, from the perspective of any given virtual machine, the hypervisor provides the illusion that the virtual machine is interfacing with a physical resource, even though the virtual machine only interfaces with the appearance (e.g., a virtual resource) of a physical resource. Examples of physical resources including processing capacity, memory, disk space, network bandwidth, media drives, and so forth.

In some embodiments, software according to the present disclosure is operable offline, on a computer, on a server, on a cloud-based system and/or on a portable computing device. In some embodiments, the image processor is part of the CT scanner, CT scanner workstation or an image post-processing workstation. In some embodiments, the image display unit (e.g. 116) comprises, for example, a computer monitor, a television, and/or another display screen, as known in the art.

In certain embodiments, the image data storage unit (e.g. data store 120) comprises a form of memory that is accessible via a computer. For example, in certain embodiments, the data storage unit comprises a hard drive, a removable disk, cloud-based storage, or any other memory unit known in the art.

The methods of the present disclosure may be carried out on an image processing system. In certain embodiments, the image processing system comprises at least one of a digital capture apparatus (e.g. 118), an image processor (e.g. 106), an image display unit (e.g. 116) and/or an image data storage unit (e.g. 118). In certain embodiments, the user 117 may desire to apply the colorization methods to an entire image, to a set of images, or, more preferably, to a segmented region of interest, leaving other pixels in grayscale. A specific region on the images is segmented either manually or by automated methods.

A thresholding step may be used to select a region of interest. In a thresholding step, a user (e.g. 117) may select a region of interest in one or more segments of an image by identifying pixel intensities within a specified range. In some embodiments, the user may select and/or segment a region of interest manually, for example, in a free-form manner via use of a function of the image processing unit. Alternatively, the region of interest may be selected and/or segmented automatically, for example, upon instruction to and action by the image processing unit. In some embodiments, the selection and/or segmentation may be conducted on a single image; however, in certain embodiments, the selection/segmentation is conducted on multiple images concurrently. In certain embodiments, a thresholding step may be applied to the digital image data and/or to any subset thereof.

In some embodiments of the methods of the present disclosure, a mask of a region of interest is created. In certain embodiments, once the region of interest is identified, subsequent colorization steps are applied to the region of interest. In another embodiment, the colorization steps are applied to an entire image and/or to an image data set.

Moreover, a color spectrum that assigns multiple different colors to a defined range of pixel intensities within a segmented region of interest is provided in the methods of the present disclosure. In some embodiments, the colors of a selected color spectrum are mapped to an image and/or to a region of interest of a selected image. In certain embodiments, the selected color spectrum comprises only colors other than those provided in an unaltered image received from the image capture device. A user may alter the color spectrum to improve visualization of an image, as needed. In some embodiments, the color spectrum comprises a one or more colors. Furthermore, a user may select which color(s) to include in a particular color spectrum, and the user may define any or all of the darkness or lightness level, saturation level, and opacity level of the color(s) in a color spectrum.

A selected color may then be assigned to a color value. In some embodiments, a color value is a number. In other embodiments, the color value is a letter or other designator. In some embodiments, the color value comprises a pixel intensity value or a range of pixel intensity values. For example, in some embodiments, the color value of blue is associated with a specific pixel intensity (e.g., 75 HU) and/or to a specific range of pixel intensities (e.g. greater than or equal to 145 HU and less than 700 HU). Additional colors may be added or removed from a given color spectrum.

In certain embodiments, if two or more colors are assigned to two or more pixel intensities, respectively, the colors may be blended to and applied to undesignated pixel intensities between them. For example, if blue is assigned to a pixel intensity of 50 and red to a pixel intensity of 100, then a pixel intensity of 75 will be a 50/50 mix of blue and red. Pixel intensities closer to 50 will have more blue color, and pixel intensities closer to 100 will have more red color (e.g., in a linear fashion or in a weighted fashion). In some embodiments, pixel intensities above or below the specified range of pixel intensities are not colorized and are left in their native grayscale form.

In some clinical scenarios, only a range of pixel intensities within a segmented region will be colorized, leaving other native grayscale pixel intensities unchanged. The unchanged native grayscale pixel intensities serve as a roadmap, making it easier for the user to visualize the anatomic region of interest. In addition, limiting the colors to a segment of the image avoids distraction from other less relevant areas on the images. The choice of color is made to differentiate different bone density conditions.

For typical cross sectional digital medical images, the pixel intensities are displayed in grayscale, and the transition from black to white is gradual with incremental changes in pixel intensity. Conversely, in certain embodiments, the colorization method(s) of the present disclosure can be used to make an abrupt change in contrast between a narrow range of pixel intensities. In other words, a color spectrum of the methods of the pending claims can, but need not be, applied to an image in a manner that reflects an incremental and/or gradual change in adjacent pixel intensity. Furthermore, multiple contrast interfaces (i.e., multiple abrupt pixel intensity and/or color changes, within a narrow range of pixels intensities) are possible using multiple different colors, and certain colors can be set to correspond to specific normal and pathologic findings. As the user selects and/or alters the colors of a particular color spectrum, the changes are visible on an image display unit. Accordingly, a user may alter the selected color spectrum and/or assigned pixel intensities associated with each color until visualization and detection of normal and/or pathologic findings is optimized and/or improved.

In some embodiments, a noise reduction filter may be applied to the digital image data and/or to any selected subset or portion thereof. Further, in certain embodiments, a smoothing algorithm is applied to the digital image data. In some embodiments, the smoothing algorithm comprises a Gaussian smoothing algorithm. In certain embodiments, the smoothing algorithm is applied to the digital image data or to any portion thereof. In certain embodiments, the smoothing algorithm is applied only to the colorized pixels. The sigma value for the Gaussian smoothing algorithm may be increased or decreased by the user, thereby increasing or decreasing the amount of smoothing, until the amount of smoothing is visually optimized in the viewer. This process reduces the image noise, which is often more apparent once the pixels are colorized. The purpose of the noise reduction filter and smoothing algorithm is to reduce image noise and further improve visualization of normal and pathologic findings on the color enhanced images. The noise reduction filter and smoothing algorithm also improve homogeneity of the image and improve visualization of the average bone density.

In some embodiments, the methods of the present disclosure include a step of receiving digital image data obtained by an image capture device in an image processor, wherein the digital image data comprises at least one image. The digital image data may be collected, transmitted, and/or stored. Additionally, the digital image data may be obtained by a digital image capture device and/or received in an image processing unit. In some embodiments, the digital image data may be transmitted and/or received in real time.

In some embodiments, the methods of the present disclosure include a step of analyzing the digital image data with the image processing unit to identify a region of interest of an image represented by the digital image data. And in certain embodiments, analyzing the digital image data comprises determining at least one statistical measure of the digital image data. In certain embodiments, the region of interest is identified manually, and in some embodiments, the region of interest is identified automatically by the image processing unit. The region of interest may include image data comprising, for example, images of a cervical spine, thoracic spine, lumbar spine, total spine, any partial component of the spine, the vertebral bodies, the cortex of the spine, or the trabecular bone of the spine.

In some embodiments, when selecting a preferred color spectrum, a user measures the pixel intensities in the spine or segmented region of interest. The measurement is most commonly an arithmetic mean pixel intensity of the organ of interest, but the statistical measurement can be a median value, variance or higher order statistical analysis. In certain embodiments, the measurement is limited to the segmented region of interest, thereby excluding other regions of the images. The measurement may be made on one or more images and include all pixels in the segmented region, but more commonly is an assessment of pixels within a limited range of pixel intensities. The purpose of performing the statistical analysis on a limited range of pixel intensities is to exclude signal from noise and from structures that are not of interest, so that the optimal color spectrum can be selected. The statistical measurement may be limited to a single image slice but is more commonly made on multiple slices, using an arithmetic mean of the measurements to derive a final value.

In some embodiments, statistical measurements are rounded to the nearest integer. Further, a user has the option to limit the statistical measure to a circular region of interest that can be manually placed on the images. The size of the circular region of interest can be altered as desired by the user. This allows the user to limit the statistical measurement to an organ, tissue or area of interest. That region of interest may be propagated onto multiple contiguous slices and an arithmetic mean of the mean pixel intensity within each region of interest is taken as the final mean pixel intensity.

In certain embodiments, the methods of the present disclosure include a step of obtaining a pixel value contained in the digital image data. The step of obtaining a pixel value contained in the digital image data may include, for example, calculating a pixel value from the digital image data and/or measuring a pixel value from the digital image data.

In certain embodiments, the methods of the present disclosure include a step of producing a colorized image (e.g. 115). In some embodiments, the colorized image is produced by replacing at least one pixel in at least one image with a corresponding colored pixel. And in some embodiments, the step of producing a colorized image comprises colorizing at least one pixel in at least one image. In certain embodiments, the at least one pixel is colorized with the at least one related color of an established color spectrum.

In some embodiments, a color spectrum is selected based on and/or related to a statistical measurement of pixel intensities in a region of interest. In certain embodiments, a color spectrum is stored by a data storage unit. And in some embodiments, the color spectrum is saved in a bank and/or data storage area (e.g. 120). In certain embodiments, the data storage unit comprises a data storage area. Indeed, the steps of the methods of the present disclosure include a number of different options, as described, so that the user can optimize the colorization and/or noise reduction for multiple clinical indications and multiple image data sets.

Some embodiments of the methods of the present disclosure include a step of generating a bank of color spectra using an optimized/selected color spectrum as a reference. For all possible statistical measurements of the pixel intensities in a segmented region of interest (which may be rounded to the nearest integer), a unique color spectrum may be generated and assigned according to a given statistical measurement value. In certain embodiments, each color spectrum in a bank of color spectra is designed to fit one statistical measurement in the segmented region of interest. For each new color spectrum that is generated, the pixel values assigned to colors in the selected color spectrum are adjusted upward or downward in proportion to a statistical measurement, though not all colors need to be shifted.

Color spectra may be further optimized and/or refined so that the statistical measure(s) of the pixel intensities in a region of interest correspond to a color spectrum that has a similar look on a new image data set. In some embodiments, a standardized color spectrum is applied to any image data set, despite variability in pixel intensities across a population of patients and despite different statistical measures of the region(s) of interest. The final colorized images may, in some embodiments, be viewed with software but can also be exported as a stack of images. In an embodiment, the final colorized images may be exported in DICOM format. The exported images can be uploaded to a picture archiving and communications system (PACS) for viewing, interpretation, and storage. In certain embodiments, the entire standardization and colorization process of the present disclosure may be fully automated and run on the image scanner computer platform or run offline on a computer, server, cloud-based system or portable computing device. The final colorized images may be integrated with the PACS. Moreover, in some embodiments, the colorized images may be interpreted in parallel, in side-by-side fashion, with the native grayscale images.

In some embodiments, the methods of the present disclosure are useful, for example, for colorizing, displaying and/or visualizing CT images of the spine to evaluate spinal bone density. In some embodiments, the trabecular bone can be automatically segmented using the surrounding cortical bone as a landmark to generate a mask. A statistical measure of the image pixel value(s) in the trabecular bone of the vertebral bodies is used to determine and apply at least one of a noise reduction filter, a smoothing algorithm and a specific color spectrum to the image data. As such, the methods of the present disclosure can facilitate the improved viewing and detection of, for example, abnormal vs. normal bone density or osteoporosis, low bone density, or normal bone density, particularly as compared to grayscale medical images.

In certain embodiments, the methods of the present disclosure are useful for improving visualization of CT images of the femoral neck to evaluate femoral neck bone density. In some embodiments, a statistical measure of the image pixel value(s) in the cortex and trabecular bone of the femoral neck is used to determine and apply at least one of a noise reduction filter, a smoothing algorithm and a specific color spectrum to the image data. Indeed, in some embodiments, images of a femoral neck are colorized, so as to facilitate improved viewing and detection of normal bone density and/or low bone density or osteoporosis, particularly as compared to grayscale medical images.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims. It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of opportunistic bone density screening, the method comprising:
    receiving, at an image processor, one or more portions of computed tomography (CT) image data obtained during a CT scan of a clinical indication unrelated to bone density using an image capture device, the CT image data including an image of at least a portion of a patient's body comprising a bone;
    processing the CT image data with the image processor to obtain a specified type of image relevant for that portion of the patient's body;
    identifying an attenuation value for one or more pixels in the processed image associated with the bone;
    providing a color palette comprising one or more colors, wherein the one or more colors are each related to a specific range of attenuation values, and wherein each specific range of attenuation values corresponds to one or more different bone density conditions; and
    mapping the provided color palette to the processed image according to the identified attenuation values to opportunistically screen for abnormal bone density conditions.

2. The method of claim 1, wherein the CT image data comprises digital CT image data, and wherein the digital CT image data comprises at least one medical image.

3. The method of claim 2, wherein processing the CT image data comprises applying a smoothing algorithm.

4. The method of claim 2, wherein the specified type of image relevant for the portion of the patient's body comprises a straightened sagittal image of the patient's midline spine.

5. The method of claim 4, wherein mapping the provided color palette to the processed image comprises mapping the color palette to a straightened thick slab sagittal image of the patient's midline spine to screen for abnormal bone density conditions.

6. The method of claim 1, further comprising producing at least one colorized medical image using the determined mapping.

7. The method of claim 6, further comprising displaying the at least one colorized medical image on a display.

8. The method of claim 1, further comprising processing the CT image data with the image processor to segment a region of interest including the patient's spine.

9. The method of claim 8, wherein the color palette is mapped to a segmented region of interest of the patient's spine.

10. The method of claim 8, wherein processing the CT image data comprises applying at least one of a noise reduction filter and a smoothing algorithm.

11. The method of claim 10, wherein at least one of the noise reduction filter and the smoothing algorithm is applied only to the segmented region of interest.

12. A computer system for opportunistic bone density screening using digital computed tomography (CT) image data, the computer system comprising:
    one or more processors; and
    one or more computer readable hardware storage devices, wherein the one or more computer readable hardware storage devices comprise computer executable instructions executable by at least one of the one or more processors to cause the computer system to perform at least the following:
        receive, at an image processor, digital CT image data obtained by a digital image capture device, wherein the digital CT image data comprises at least one medical image;
        process the digital CT image data with the image processor to obtain a straightened sagittal image of the midline spine such that processing the digital CT image comprises removing a spinal curvature by aligning vertebrae in a co-localized plane;
        identify an attenuation value for one or more pixels in the at least one medical image;
        provide a color palette comprising one or more colors, wherein the one or more colors are each related to a specific range of attenuation values, and wherein each specific range of attenuation values corresponds to one or more different bone density conditions; and
        map the selected color palette to the straightened thick slab sagittal image of the spine to screen for abnormal bone density conditions.

13. The computer system of claim 12, wherein the computer, when processing the CT image data, is caused to apply a smoothing algorithm.

14. The computer system of claim 12, further comprising producing at least one colorized medical image using the determined mapping and displaying the colorized medical image on a display.

15. The computer system of claim 14, wherein at least one abnormal bone density condition is defined as greater than 30 Hounsfield Units (HU) and less than 145 HU, and wherein normal bone density is defined as greater than or equal to 145 HU and less than 700 HU.

16. The computer system of claim 14, wherein at least one abnormal bone density condition is defined as greater than 30 HU and less than 95 HU, and wherein normal bone density is defined as greater than or equal to 95 HU and less than 700 HU.

17. The computer system of claim 14, wherein osteoporosis is defined as greater than 30 HU and less than 95 HU, low bone density is defined as greater than or equal to 95 HU and less than 145 HU, and normal bone density is defined as greater than or equal to 145 HU and less than 700 HU.

18. The computer system of claim 14, wherein abnormal bone density has a first specified color, and normal bone density has a second specified color.

19. A computer system for opportunistic bone density screening, comprising:
  a receiver configured to receive one or more portions of computed tomography (CT) image data obtained during a CT scan of a clinical indication unrelated to bone density using an image capture device, the CT image data including an image of at least a portion of a patient's body comprising a bone;
  an image processor configured to process the CT image data to obtain a specified type of image relevant for that portion of the patient's body;
  an attenuation determining module executed at one or more processors configured to identify an attenuation value for one or more pixels in the processed image associated with the bone;
  a color palette provider configured to provide a color palette comprising one or more colors, wherein the one or more colors are each related to a specific range of attenuation values, and wherein each specific range of attenuation values corresponds to one or more different bone density conditions; and
  a mapping module executed at the one or more processors configured to map the provided color palette to the processed image according to the identified attenuation values to opportunistically screen for abnormal bone density conditions.

20. The computer system of claim 19, wherein the computer is configured to apply a smoothing algorithm when processing the CT image data.

21. The computer system of claim 19, wherein processing the tomography image data to obtain a specified type of image relevant for that portion of the patient's body includes obtaining a thick slab sagittal image of the patient's midline spine.

22. The computer system of claim 19, wherein the image data comprises medical images of a plurality of patients.

23. The computer system of claim 19, wherein the image processor comprises a CT scanner or image workstation.

* * * * *